(12) United States Patent
Huckle et al.

(10) Patent No.: US 7,108,721 B2
(45) Date of Patent: Sep. 19, 2006

(54) TISSUE REGRAFTING

(75) Inventors: James William Huckle, Northallerton (GB); Melissa Anderson, Hull (GB); Allen E. Goodship, Herts (GB); Venkatram R. Shastri, Lower Gwynedd, PA (US)

(73) Assignee: Massachusetts Institute of Technology, Cambridge, MA (US)

( * ) Notice: Subject to any disclaimer, the term of this patent is extended or adjusted under 35 U.S.C. 154(b) by 253 days.

(21) Appl. No.: 10/275,618

(22) PCT Filed: May 10, 2001

(86) PCT No.: PCT/US01/15070

§ 371 (c)(1),
(2), (4) Date: Jul. 2, 2003

(87) PCT Pub. No.: WO01/85226

PCT Pub. Date: Nov. 15, 2001

(65) Prior Publication Data

US 2004/0010320 A1    Jan. 15, 2004

(30) Foreign Application Priority Data

May 11, 2000    (GB) .............................. 0011244.1

(51) Int. Cl.
*A61F 2/36*    (2006.01)
*A61F 2/08*    (2006.01)
*A61F 2/28*    (2006.01)

(52) U.S. Cl. .................... 623/23.74; 623/23.76
(58) Field of Classification Search ............. 623/23.72, 623/23.76, 13.11, 14.12, 16.11
See application file for complete search history.

(56) References Cited

U.S. PATENT DOCUMENTS

| | | | | |
|---|---|---|---|---|
| 4,467,478 A | * | 8/1984 | Jurgutis ................... | 623/13.17 |
| 4,563,350 A | * | 1/1986 | Nathan et al. .............. | 424/549 |
| 4,919,667 A | * | 4/1990 | Richmond ................ | 623/14.12 |
| 5,855,610 A | | 1/1999 | Vacanti et al. | |
| 6,077,989 A | * | 6/2000 | Kandel et al. ........... | 623/13.17 |
| 6,287,340 B1 | * | 9/2001 | Altman et al. ........... | 623/13.11 |

FOREIGN PATENT DOCUMENTS

WO    WO 97/40137    10/1997

* cited by examiner

*Primary Examiner*—Thomas Barrett
(74) *Attorney, Agent, or Firm*—Fish & Richardson P.C.

(57) ABSTRACT

The present invention is based on the discovery of new methods for obtaining a tissue graft. The method can be carried out, for example, by implanting a biocompatible scaffold into a mammal and then removing the scaffold from the mammal. The scaffold is implanted in direct contact with (i.e. physically touching over at least a portion of its external surface), or adjacent to (i.e. physically separated from) mature or immature target tissue, for a period of time that is sufficient to allow cells of the target tissue to associate with the scaffold. The invention also features grafts generated by the methods described herein and methods for using those grafts to treat patients who have a defect in a target.

17 Claims, 4 Drawing Sheets

TISSUE REGRAFTING

TECHNICAL FIELD

This invention relates to the field of tissue reconstruction and is particularly concerned with the treatment of connective tissues such as skin, ligament, cartilage, bone, and tendon.

BACKGROUND

Traditionally, two types of surgical procedures have been used to repair injured connective tissue. In the first, a naturally occurring tissue is used as the basis for the graft, and in the second, a synthetic material is used. When a naturally occurring tissue is grafted, it is often one that is harvested from the injured patient (i.e., an autograft), but the extent to which autografts may be made is limited by the amount of tissue available. In addition, donor site morbidity and necrosis of the implanted graft are problems that have not yet been overcome. As alternatives, one can graft allogenic tissue (i.e., tissue taken from an individual of the same species as the recipient but with different hereditary factors) or xenogenic tissue (i.e. tissue taken from a donor who is not of the same species as the recipient). Use of these tissue types eliminates the problems associated with harvesting tissue from the injured patient, but there may be a risk that the graft will transmit disease. The injured patient may also mount an immune response that leads to graft rejection. Thus, allogenic and xenogenic tissues are used in only a limited number of reconstructive surgeries.

While synthetic materials and devices are not as susceptible to acute rejection, they have generally failed to show successful long-tern results. For example, devices used for the replacement of ligaments commonly fail over a 2–10 year period due to synovitis, loosening, or implant failure. Following implantation, continuous loading of the device and abrasion against joint tissues causes wear, creep, and fatigue, which worsen until the device eventually fails.

Some synthetic devices have been designed to encourage tissue ingrowth, as it was thought that this would strengthen the device. Unfortunately, the ingrowth observed has been disorganized and not of a sufficient quality or quantity to lend the anticipated benefit In addition to the traditional surgical approaches discussed above, tissues have been repaired by tissue engineering, which is a multidisciplinary science that utilize principles from the life sciences, engineering, and other disciplines to create cellular constructs for transplantation. These constructs are generally created in vitro. However, in some circumstances, they are also created in vivo, where the body is effectively used as a bioreactor. When this is done, the constructs are seeded with cells, such as mesenchymal cells, either before or after they are implanted (see, e.g., U.S. Pat. No. 5,855,610). Ibarra et al. (see "Transplantation of Tissue Engineered Meniscus in Sheep", 44th Meeting, Orthopaedic Research Society, March 16–19, New Orleans, La., USA) also report a method involving implantation of a scaffold with a view to generating a tissue-engineered implant. This method also comprises the step of seeding the scaffold with cells prior to implantation.

SUMMARY

The present invention is based on the discovery of new methods for obtaining a tissue graft (which may also be referred to herein as an "implant"). The method can be carried out, for example, by implanting a biocompatible scaffold (i.e. a three dimensional, partially porous structure that fails to cause an acute reaction when implanted into a patient) into a mammal and then removing the scaffold from the mammal. The scaffold is implanted in direct contact with (i.e. physically touching over at least a portion of its external surface), or adjacent to (i.e. physically separated from) mature or immature target tissue, for a period of time that is sufficient to allow cells of the target tissue to associate with the scaffold. The tissue graft includes the removed scaffold and the associated cells of the target tissue.

"Target tissue" is tissue of any type that a graft is generated to replace. For example, where a patient has torn or otherwise damaged a ligament, and that ligament is targeted for replacement with a graft created by the methods described herein, the target tissue is ligament. When the patient has damaged cartilage, the target tissue is cartilage; when the patient has a damaged tendon, the target tissue is tendon; and so forth. The target tissue is "mature" when it includes cells and other components that are naturally found in fully differentiated tissue (e.g. a recognizable ligament in an adult mammal is a mature target tissue). The target tissue is "immature" when it includes cells that have not yet differentiated into, but which will differentiate into, mature cells (e.g., immature target tissue can contain mesenchymal stem cells, bone marrow stromal cells, and precursor or progenitor cells). Target tissue is also "immature" when it contains cells that induce immature cells to differentiate into cells of a mature target tissue or when it contains cells that sustain mature cells (these events can occur, for example, when cells secrete growth factors or cytolines that bring about cellular differentiation or sustain mature cells). Thus, the methods of the invention can be carried out by implanting a biocompatible scaffold in direct contact with, or adjacent to, target tissue or tissue that includes cells that can produce target tissue (by, for example, the processes described herein—differentiation or through the action of growth factors or cytokines).

Without adopting any one theory regarding the underlying mechanisms of action, it is believed that the graft will include cells of a mature target tissue not only because mature cells of the target tissue migrate onto (and into) the scaffold, but also because immature target tissue differentiates or induces cells associated with the scaffold to differentiate along a particular pathway. When cells produce target tissue, one or more of these mechanisms may be responsible. When, for example, an implant comprising a scaffold and tissue derived from the periosteum is implanted into an articular cartilage-defect (or when an implant comprising a scaffold and tissue derived from a patellar tendon is implanted into an anterior cruciate ligament (ACL) defect), it is believed that a mixture of these processes, i.e. differentiation of cells already present and population with new cells and differentiation of those cells, is occurring to generate target tissue (here, articular cartilage tissue and ACL-tissue, respectively). The type of tissue that, in any given case, is capable of producing target tissue is known to surgeons, who perform grafting (e.g., autografting) procedures, and others of ordinary skill in the art. The term "target tissue" can be used interchangeably with the term "tissue of the target type."

As described further below, the scaffold can be fashioned from woven, non-woven, knitted, braided or crocheted material, foam, sponge, or dendritic material, any of which can be either bioresorbable (i.e., of a material that it breaks down over time (e.g. 3–5 years) due to the biochemical action of the body) or non-bioresorbable. For example, the material of the scaffold can include a polymer or copolymer such as those formed by a hydroxy acid (e.g., lactic acid), a glycolic acid, caprolactone, hydroxybutyrate, dioxanone, an orthoester, an orthocarbonate, or an aminocarbonate. Alternatively, or in addition, the material of the scaffold can include collagen, cellulose, fibrin, hyaluronic acid, fibronectin, chitosan, or a devitalised graft (e.g., a devitalized xenograft or allograft). Ceramics, such as those formed with a mono-, di-, octa-, α-tri-, β-tri, or tetra-calcium phosphate, hydroxyapatite, fluoroapatite, calcium sulphate, calcium fluoride, or calcium oxide can also be used in the scaffold. Non-bioresorbable materials include, but are not limited to, polyalkylene terephthalate, polyamides, polyalkenes, poly(vinyl fluoride), polytetrafluoroethylene carbon fibres, natural or synthetic silk, carbon fibre, and glass.

The scaffold can assume the shape of any biological tissue (e.g. the scaffold can assume the shape of a target tissue such as cartilage, ligmant, tendon, or bone). For example, where the scaffold has a rope-like structure, the graft that is generated will have a rope-like shape; where the scaffold has a meniscus-like structure, the graft that is generated will have a meniscal shape.

In addition to the materials described above, the scaffold can include biological molecules, such as a polypeptide growth factor (e.g., a transforming growth factor, a bone morphogenetic protein (BMP), a cartilage-derived morphogenic protein, a growth differentiation factor, an angiogenic factor, a platelet-derived growth factor, a vascular endothelial growth factor, an epidermal growth factor (EGF), a fibroblast growth factor, a hepatocyte growth factors, an insulin-like growth factor, a growth hormone, an interleukin, a connective tissue growth factor, or a parathyroid hormone-related protein).

The scaffold can have an open volume. For example, approximately 30–99% of the total volume of the scaffold (e.g. 35, 40, 50, 60, 75, 80, 90, or 95%) can be an open volume.

In one embodiment, the scaffold can include an elongated fabric tape (e.g., one containing poly(lactic acid) fibres) and a non-woven felt (e.g., one containing poly(glycolic acid) fibres). The non-woven felt can be stitched onto one of the surfaces of the fabric tape and, where desired, the resulting structure can be helically wound.

The scaffold, prior to implantation, can be one that bears no cells. Similarly, the scaffold, following removal from the mammal, can be one that is suitable for use as a graft without the addition of any other cell type. Of course, one can "seed" the scaffold at any point during the production of the graft (i.e. before, during, or after implantation in a mammal).

The invention also features tissue grafts obtained by a method described herein and methods of treating a mammal that has a tissue defect by implanting the tissue graft into the mammal at the site of the tissue defect (e.g. a defect of a tendon or ligament such as the natural cruciate ligament or natural collateral ligament). The mammal that has the tissue defect and the mammal from which the tissue graft is obtained can be the same mammal or the same type of mammal (e.g. one human patient can have a tissue defect that is treated with a graft generated in another human). Alternatively, the mammal that has the tissue defect and the mammal from which the tissue graft is obtained can be different types of mammals (e.g., a human patient can have a tissue defect that is treated with a graft generated in another primate, a cow, a horse, a sheep, a pig, or a goat).

Once obtained, the graft can be implanted in a mammal at the site of a tissue defect by any surgical technique. For example, the tissue graft can be sutured, pinned, tacked, or stapled into a mammal at the site of a tissue defect. In one embodiment, the graft is implanted by attaching a first portion of the graft to a first support structure at the site of the tissue defect and attaching a second portion of the graft to a second support structure at the site of the tissue defect, such that the graft connects the first support structure to the second support structure. In the event the first support structure is the tibia, the second support structure can be the femur. In the event the first support structure is a first articular surface of a joint (e.g. a shoulder, wrist, elbow, hip, knee or ankle joint), the second support structure can be a second articular surface of the same joint (i.e., the shoulder, wrist, elbow, hip, knee, or ankle joint, respectively). As used herein, the term "adjacent to" means that the scaffold is separated from the tissue of the target type, or tissue comprising cells that can produce tissue of the target type or both, if both are present, by a distance of up to 10 mm and preferably less than 5 mm.

Practicing a related aspect of the invention, one can generate an implant that includes a biocompatible scaffold and target tissue (mature target tissue or tissue that includes cells that can produce tissue of the target type) by (a) surgically implanting the scaffold into a site in a mammalian organism such that the scaffold is in direct contact with, or adjacent to, target tissue (mature target tissue or tissue that includes cells that can produce the target tissue); (b) allowing cells of the target tissue (mature target tissue or tissue that includes cells that can produce the target tissue) to infiltrate the scaffold and lay down tissue, and (c) surgically removing the implant created thereby. As noted, the scaffold can include woven, nonwoven, knitted, braided or crocheted material foam, sponge, dendritic material or a mixture thereof. The bioresorbable and non-bioresporbable materials described herein are useful in this method (the bioresorbable materials used can be those that lose less than 5% of their weight when implanted in vivo for a 12-week period), as are the biological materials (such as polypeptide growth factors).

In another aspect, the invention features a method for treatment of a tissue at a selected site by (a) placing a scaffold into a target site in a mammalian subject such that the scaffold is in direct contact with, or adjacent to, tissue of a target type (or tissue comprising cells which can produce tissue of the target type, or both) so that cells of the target type (or cells that can produce tissue of the target type, or both) can infiltrate the scaffold and lay down tissue and thereby generate an implant; (b) removing the implant; and (c) implanting the implant at a selected site in the mammalian subject. The "placing" can include attaching the scaffold into the target site. Further, the "attaching" can be performed by suturing, pinning, tacking, or stapling the scaffold into the target site. Here again, the target tissue can be a tendon (e.g., the patellar tendon), ligament (e.g., the ACL), cartilage (e.g. a rib cartilage), or bone (e.g., periosteum or perichondrium). Implantation of the implant can include attaching a first portion of the implant to a first support structure at the selected site and attaching a second portion of the implant to a second support structure at the selected site, such that the implant connects the first support structure to the second support structure. According to any of these methods, the scaffold can be unseeded with tissue cells or seeded with cells of the target tissue (or cells that produce target tissue).

The end-point of the above-defined methods (i.e. the point at which the implant (scaffold plus ingrown tissue) is removed), depends upon factors such as the nature of the target tissue (or the tissue comprising cells that can produce target tissue) and the desired final application of the resulting implant. One end-point is an implant comprising a substantially filly infiltrated scaffold (i.e. an implant that comprises substantially only scaffold and tissue (i.e. cells, extracellular matrix, and growth factors) and no (or no significant) gaps between. A fully infiltrated scaffold can be generated in 2–12 weeks from the time the scaffold is implanted. Under certain circumstances, a less than fully infiltrated implant may suffice. In the case of generating tendon implants, an alternative time-point for removal of the implant is the time at which less than 85% and preferably less than 80% of the dry weight of the implant is made up of the scaffold (i.e., more than 15% and preferably more than 20% of the dry weight of the scaffold is made up of ingrown components (such as collagen, DNA and glycosaminoglycans or GAGS)).

The details of one or more embodiments of the invention are set forth in the accompanying drawings and the description below. Other features, objects, and advantages of the invention will be apparent from the description and drawings, and from the claims.

DETAILED DESCRIPTION

Methods for obtaining a tissue graft, and the graft obtained thereby, are described further below. These methods can be used to generate a wide variety of tissue grafts, which can each include cells of a target type or cells of a variety of target types. For example, one can graft a scaffold (e.g., a rope-like scaffold) on top of or adjacent to a tendon or ligament to allow tissue to grow onto (or into) the scaffold. The graft generated (i.e. the scaffold and the tissue it bears at the end of the implantation period) can then be removed and grafted into a joint (e.g., a knee joint) to repar a ruptured or otherwise damaged ligament (e.g., the ACL). In another case, one can place a scaffold (e.g., a meniscal-shaped scaffold) on top of or adjacent to a tendon or ligament (e.g., the patellar tendon) to generate a meniscal-shaped implant comprising collagenous tissue. In yet another case, one can place a scaffold onto or adjacent to rib cartilage (i.e., the periosteum or perichondrium) to allow ingrowth of tissue prior to regrafting the resulting implant into the articular surface of a knee joint. Similarly, one can generate a graft for bone repair. To create such a graft, the scaffold could be placed or grafted under the periosteum, adjacent to the cortical bone. If required, holes could be drilled through the cortical bone and into the marrow space to allow passage of cells from the bone marrow into the scaffold. The periosteum or marrow cells can infiltrate the scaffold and lay down a tissue prior to regrafting into the site of a bone defect.

As described herein, the scaffold can consist of bioresorbable or non-bioresorbable material. If the scaffold consists of a single bioresorbably material, it is, preferably, one that does not significantly resorb during the period of time that tissue is being laid down on or within it. Such scaffolds will generate a graft that includes living cells and essentially retain their shape and mechanical integrity. For example, scaffolds can be used that lose less than 5% of their weight when implanted in vivo for a 12-week period. In some instances it may be preferably to use scaffolds containing bioresorbably materials that lose less than a 2% of their weight during the same period. If the scaffold is constructed with two or more bioresorbable materials, it may be preferable to select the bioresorbable material that provides the scaffold with its structural integrity according to these criteria.

A wide range of bioresorbable materials is known, with differing in vivo resorption times. Moreover, the resorption time of a single material itself can also vary significantly with molecular weight. By blending or copolymerising different bioresorbable materials and/or by modifying the molecular weights of the materials, it is possible to tailor the resorption time of the bioresorbable material to the requirement at hand.

The bioresorbable materials useful in the present invention can include bioresorbable polymers or copolymers that include the following monomers or mixtures of polymers and/or copolymers formed thereby: hydroxy acids, particularly lactic acid, glycolic acid; caprolactone; hydroxybutyrate; dioxanone; orthoesters; orthocarbonates; aminocarbonates.

The bioresorbable materials can also include natural materials such as collagen, cellulose, fibrin, hyaluronic acid, fibronectin, chitosan or mixtures of two or more of these materials. The bioresorbable materials may also comprise devitalised xenograft and/or devitalised allograft.

Bioresorbable ceramics can also be included within the scaffold. Bioresorbable ceramics which may be used include mono-, di-, octa-, $\alpha$-tri-, $\beta$-tri and tetra-calcium phosphate, hydroxyapatite, fluoroapatite, calcium sulphate, calcium fluoride, calcium oxide or mixtures of two or more of these materials.

Preferred bioresorbable materials according to the invention comprise poly(lactic acid), poly(glycolic acid), polydioxanone, polyhydroxybutyrate and poly(trimethylene carbonate) or mixtures thereof. Poly(lactic acid) has good mechanical strength and does not resorb quickly. Thus, its mechanical properties can be retained for a time sufficient for tissue ingrowth to occur (at which point the tissue can assume some, if not all, of the load-bearing function of the scaffold (see A. G. A. Coombes and M. C. Meikle, "Resorbable Synthetic Polymers as Replacements for Bone Graft", Clinical Materials 17:35–67, 1994). Samples of poly(lactic acid) have been shown to lose only one or two percent of their weight over a 12-week trial.

Appropriate non-bioresorbable materials include polyesters, particularly aromatic polyesters, such as polyalkylene terephthalates, like polyethylene terephthalate and polybutylene terephthalates; polyamides; polyalkenes such as polyethylene and polypropylene; poly(vinyl fluoride), polytetrafluoroethylene carbon fibres, silk (natural or synthetic), carbon fibre, glass, and mixtures of these materials. An advantage of non-bioresorbable materials is that they essentially retain their initial mechanical properties. Thus, their strength does not lessen over time.

As the scaffold is at least partially porous, it allows tissue in-growth. When the scaffold contains interconnected pores that are evenly distributed, cells can infiltrate essentially all areas of the scaffold during the period of implantation. The pore diameter is determined by, inter alia, the need for adequate surface area for tissue in-growth and adequate space for nutrients and growth factors to reach the cells. The percentage open volume of the scaffold is selected by balancing the needs for "open" volume, which allows and adequate number of cells and sufficient nutrients to permeate quickly through the structure and desirable mechanical properties (such as a high compressive modulus in the case of articular cartilage implants). Advantageously, to achieve these objectives, the percentage open volume will be in the range 30–99% and preferably in the range 40–99%.

The scaffold according to the invention may comprise a woven, non-woven (fibrous material), knitted, braided or crocheted material, a foam, a sponge, a dendritic material, or a mixture of two or more of these. Where the scaffold includes a knitted or woven material, it may be arranged as a spacer fabric, which can easily be adjusted to give a specific architecture. This allows properties (like percentage open volume and strength) to be accurately tailored to the specific application.

The scaffold can be planar in form, cut or otherwise formed, if necessary, to an appropriate shape. For example, the scaffold can form a quadrilateral, circle, triangle, or other geometric shape in plan view. If the scaffold is planar, it can include a single layer or a plurality of superimposed layers. If a plurality of layers is employed, they may be identical or non-identical (e.g., each layer can have a content and shape that differs from that in some or all of the other layers). Other alternatives include a planar scaffold, having one or more layers (identical or non-identical) that are: helically-wound; folded into a serpentine or "concertina"-type of arrangement, whereby the juxtaposed curves of the "concertina" are attached to one another; or rolled into a tube or a plurality of such tubes of diminishing size, concentrically arranged.

Where the target tissue is a ligament (e.g., the ACL), the scaffold can include an elongate fabric tape comprising both warp and weft strands. The tape can include first elongate elements that can, in turn, include woven, non-woven, knitted, braided or crocheted material. Advantageously, the first elongate elements include braided material, which has a favourable load to elongation relationship (i.e., high strength incorporating sufficient elasticity). Other materials, such as single fibres, can fatigue and break in vivo.

If the first elongate elements include braided material, the pick rate of the braided material may advantageously be in the range from 10 to 30 picks/cm and comprise between 4 and 64 yarns (e.g., between 8 and 64 yarns). The number of filaments per yarn is advantageously in the range 30 to 150, and the filaments preferably have a diameter in the range 8–20 μm.

The first elongate elements can be independently translatable in the warp direction with respect to each other and with respect to the weft strands, but maintained in a spaced apart relationship with respect to each other in the weft direction.

The tape included with the scaffold can be heat sealed or sealed with a binder to prevent fraying at the edges. It is preferred to heat seal the tape when it includes independently translatable first elongate elements (to help prevent them from becoming detached).

The first elongate elements may be maintained in a spaced apart relationship by the weft strands alone or, in addition, by non-translatable second elongate elements interspersed between the translatable first elongate elements. The second elongate elements can include chain stitched, woven, non-woven, knitted, braided or crocheted material. Advantageously, the second elongate elements include chain-stitched material. A line of chain stitches has the advantage of fulfilling the task of being a spacer element while not occupying much space itself.

It is particularly preferred that the elongate fabric tape include an upper and a lower layer, each layer including an open mesh structure comprising warp and weft yarns (the first elongate elements being laid into the structure). According to this form of the invention, the warp and weft strands of the upper and lower layers may cooperate to maintain the first elongate elements in a spaced relationship in the weft direction. This may be achieved by attaching weft strands of the upper layer to corresponding weft strands of the lower layer at positions between adjacent first elongate elements moving along the weft. Attachment may be by various methods (e.g., spot fusing or by means of a warp strand linking the upper and lower weft strands).

The scaffold can also include non-woven material, which can improve cellular in-growth. The non-woven material can be incorporated within the braided tape, as previously described, in which case it is preferably evenly distributed throughout. In this configuration, once cells infiltrate the scaffold, they proliferate more evenly throughout. Alternatively, the non-woven material can be attached to at least one of the opposing surfaces of the braided tape and preferably to both. In a further alternative, the scaffold can be encased in the second component.

The non-woven material may be dry laid, wet laid, spun laid or melt blown. Advantageously, the fibres are needled to give a random entanglement providing a large surface area for cell attachment or capture during cellular in-growth. The void fraction of the non-woven material may be in the range 50 to 99% (e.g., 90 to 99%). Typically, the non-woven material will have a density in the range 25 to 100 g/m$^2$ and staple fibre lengths in the range 40–50 mm, though values outside these ranges may also be employed. The non-woven material is typically 0.25 to 5 mm thick (e.g., 0.5 to 2 mm thick), but materials having thickness outside these ranges are also useful.

In one embodiment, the scaffold includes an elongated fabric tape comprising poly(lactic acid) fibres and a non-woven felt comprising poly(glycolic acid) fibres, the non-woven felt being stitched onto one of the opposing surfaces of the fabric tape and the resulting scaffold being spirally wound into a "Swiss Roll" with the free end being width-stitched (e.g. by pillow-stitching) to prevent unravelling.

The scaffold can include certain additional components. For example, the scaffold can include bioactive materials, such as growth factors. For example, the scaffold can contain a growth factor from the transforming growth factor β superfamily (e.g., a TGFβ or a TGFα), a bone morphogenetic protein (BMP, e.g., BMP2 or BMP4), cartilage-derived morphogenic proteins (CDMPs, e.g., CDMP-1 or CDMP-2) and growth differentiation gactors (e.g., GDF5); angiogenic factors (e.g., angiogenin), platelet-derived cell growth factor (PD-ECGF), platelet-derived growth factors (PDGFs, e.g., PDGF-A, PDGF-B, PDGF-BB), vascular endothelial growth factor (VEGF); a member of the epidermal growth factor family (e.g., EGF, TGFs and PDGFs (as mentioned above); Fibroblast Growth Factors, (e.g., BFGF); hepatocyte growth factors (HGFs); insulin-like growth factors (e.g. IGF-I and IGF-II; growth hormones (GHs); interleukins (e.g., IL-1–IL-15); connective tissue growth factors (CT-GFs); parathyroid hormone related proteins (PTHrp); and mixtures of two or more of these factors.

Hydrogels can also be included in the scaffold. For example, the hydrogel can be incorporated within and/or around the scaffold prior to implantation to facilitate the transfer of cells and other biological material (e.g., growth factors) from the surrounding tissue into the scaffold. Hydrogels comprise positively charged, negatively charged, and neutral hydrogels that can be saturated or unsaturated. Examples of hydrogels are TETRONICS™ and POLOXAMINES™, which are poly(oxyethylene)-poly(oxypropylene) block copolymers of ethylene diamine; polysaccharides, chitosan, poly(vinyl amines), poly(vinyl pyridine), poly(vinyl imidazole), polyethylenimine, poly-L-lysine, growth factor binding or cell adhesion molecule binding derivatives, derivatised versions of the above (e.g. polyanions, polycations, peptides, polysaccharides, lipids, nucleic acids or blends, block-copolymers or combinations of the above or copolymers of the corresponding monomers); agarose, methylcellulose, hydroxyproylmethylcellulose, xyloglucan, acetan, carrageenan, xanthan gum/ocust beangum, gelatine, collagen particularly Type 1), PLURONICS™, POLOXAMERS™, POLY(N-isopropylacrylmide) and N-isopropylacrylmide copolymers.

An advantage of the methods described herein is that they can avoid the necessity of seeding a scaffold with cells. This makes the procedure simpler and less time-consuming than procedures disclosed in the prior art. While seeding is not necessary, it can nevertheless be done, either prior to or after implantation. The types of cells with which the scaffold may be seeded include cells of the target tissue and cells that can produce target tissue.

The scaffold can also include a shield to exclude ingrowth of unwanted tissue phenotypes. Although it is generally beneficial to place the largest possible proportion of the surface area of the scaffold in direct contact with, or adjacent to, target tissue (mature or immature), there may be tissue types in the vicinity of the implant that will be detrimental to the formation of target tissue (e.g., tissue types that populate the scaffold but that are not, or do not produce, target tissue). A shield can be used to reduce or prevent these unwanted cells from infiltrating the scaffold. The shield can be placed around the part of the scaffold adjacent to cells of the unwanted tissue type. The shield should be too dense to allow the passage of cells, but porous enough to permit nutrients to reach the cells associated with the scaffold (and allow waste products to diffuse away). The shield may: include a non-porous barrier that allows moisture, but not cells, to reach the scaffold (e.g. by diffusion through the barrier); be impermeable to both fluid and cells, allowing neither to reach the scaffold; or it may be porous, allowing fluids and nutrients to reach cells that have moved into the scaffold from unshielded portion, but not allowing the passage of cells. The shield can be removed from the graft prior to the time the graft is implanted (i.e., prior to the time the graft is used to treat a patient with a damaged target tissue).

1. Polymer for Moisture Exchange but without Possibility of Cellular Exchange

A high moisture transmission rate polymer that lacks physical perforation may be employed, for example "HPU 25", a copolymer of Desmodur W (dicyclohexylmethane-4, 4'-diisocyanate), polyethylene glycol, ethylene glycol and water to give a copoly(ester-urea-urethane) which is an elastomer with very high moisture transmission rate and which may be cast from solution to give a conformable film 2. Polymer for Neither Fluid Nor Cellular Exchange A non-hydrophilic polymer may be employed, such as low density polyethylene, e.g. a copolymer of polypropylene glycol, diphenylmethane-4,4'-diisocyanate and ethylene glycol; hydrophobic polyurethane elastomer; hydrophobic polyester film, e.g. a copolymer of terephthalic acid with tripropylene glycol.

3. Filter or Shield that Allows Nutrient Transport but not Cell Infiltration.

Materials as described above may be employed, but with a pore size of less than 0.85 μm.

4. Scaffold Reinforcement

The scaffold can be reinforced by including a reinforcing component made, for example, from the resorbable or non-bioresorbable polymers listed above. Preferably, the reinforcing component comprises a thermosetting polymer or a solution of a thermosetting polymer, which is added to the scaffold to form strengthening bridges. More preferably, the polymer is one that thermosets at just above body temperature. A polymer of this type can fulfil a strengthening function and yet be rendered mouldable by a surgeon facilitating improved insertion of the scaffold into a defect. Most preferably, the reinforcing component comprises polycaprolactone, because this material has a melting temperature slightly above body temperature, is biocompatible, bioesorbable and may render the scaffold mouldable.

According to a second aspect of the present invention, an implant is presented comprising a biocompatible scaffold and tissue, the implant being obtainable by the above-defined methods.

According to a third aspect of the invention, a method of treatment of a mammalian organism in clinical need thereof is presented, the method comprising the step of implanting the implant obtainable by the method according to the first aspect of the invention into a tissue defect in the mammalian organism.

The follow examples illustrate various aspects of the invention.

EXAMPLE 1

Scaffold Manufacture

PLA yarn (90 filament) is twisted at 200 turns/meter ("S" direction), wound onto 16 braider spools, and braided at 1680 picks per meter. PLA yarn (40 filament) is twisted at 200 turns/meter ("S" direction) and wound onto 11 knitting spools, and two weft spools.

The scaffold is crocheted as follows:

Bar 1 Eleven ends of yarn at one per guide knitting 01/01/01/01/ at 4 gauge (needles/cm).

Bar 2 One end of yarn laying in at 1,1/1,1/(n+2),(n+2)/(n+2),(n+2); n=number of braids.

Bar 3 Ten braided ends of PLA Laying in at 00/00/00/00/ at one end per tube.

Bar 4 As bar 2, but in opposition.

Bar 5 A specially constructed unit laying in 1 mm thick PGA felt (density—1 mg/cm$^3$) behind the last guide bar.

Courses/meter are set at 535. The felt is cut slightly too wide to insert into the knitting, and the sides of the tape are tried later.

The scaffold was cut into the 280 mm lengths and held at both ends of the outer braid. The outer braid was twisted so that the scaffold rolls over itself to form a spiral section structure. The lip formed by this process was attached to the rest of the scaffold by stitching PLA fibre through the scaffold and lip along the entire length of the device.

EXAMPLE 2

Implantation of Scaffolds over Patellar Tendons

Scaffolds manufactured according to the method described in Example 1 were placed over (i.e., adjacent to) the patellar tendon in one hind limb of each of eight skeletally mature Welsh ewes. The scaffold was attached to the proximal pole of the tibial tuberosity using a small cortical screw via a stab incision. The scaffold was placed alongside the patellar tendon via a subcutaneous tunnel and attached to the proximal pole of the patella again using a small cortical screw with the knee extended to half the functional extension angle. The animals were housed extensively to allow normal functional locomotion for a post-operative period of eight weeks. The resulting grafts, which included the scaffold and tissue, were then harvested for analysis.

Figure 1:
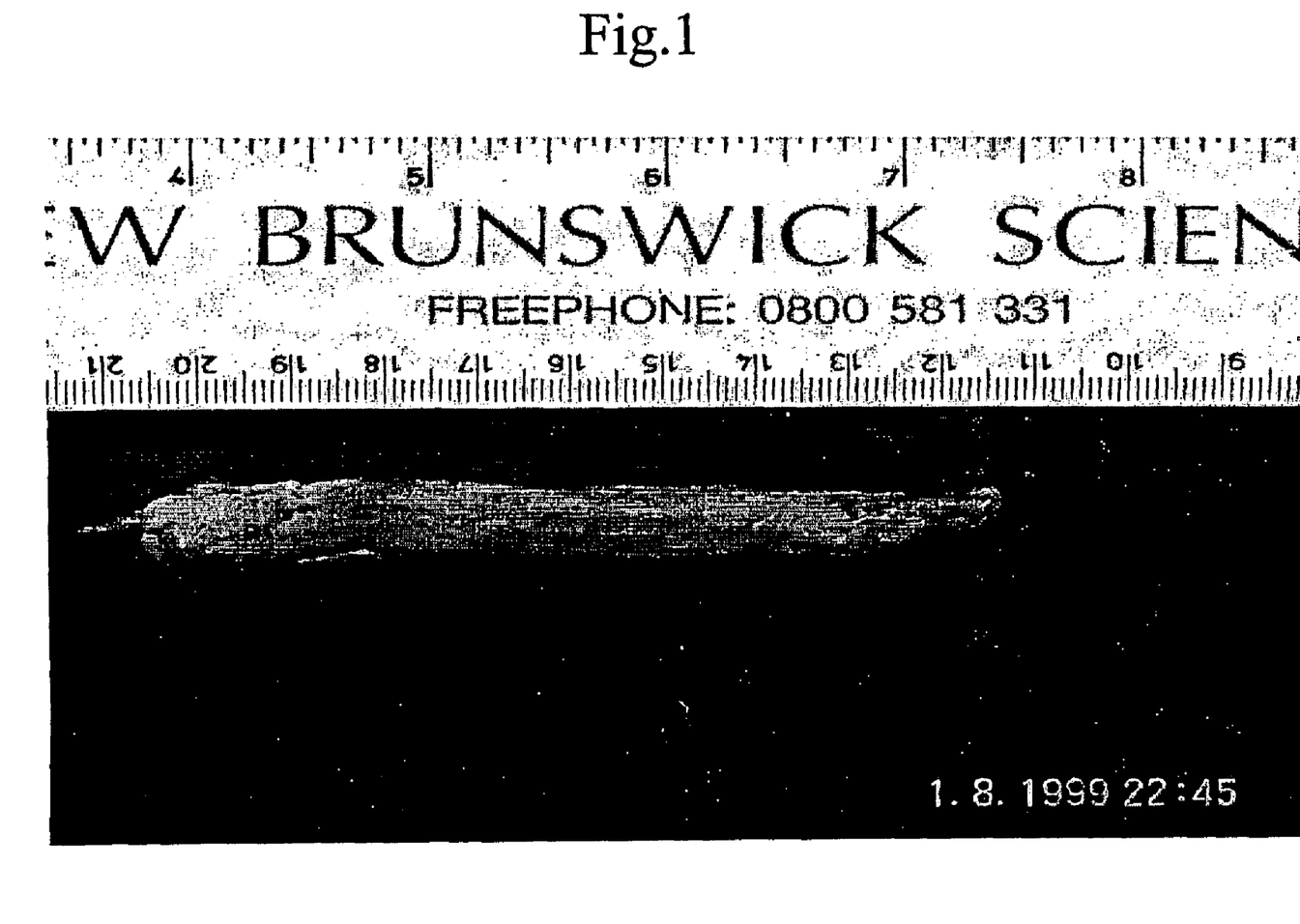
FIG. 1 is a photograph illustrating a graft generated by the method described in Example 2. The graft was formed following implantation for 8 weeks over (i.e., adjacent to) an ovine patellar tendon.

The graft obtained by the method described in Example 2 is shown in FIG. 1. The scaffold was essentially completely enveloped in tissue (tendon tissue in this case) to generate a graft that can be used as a ligament graft.

The graft was also examined histologically. Transverse sections were stained with picro-sirius collagen stain. Patellar tendon tissue could be seen ingrown among the oval-shaped braids. Blood vessels developed in the centres of the braids. This vascular tissue should be advantageous for tissues that benefit from a vascular blood supply (such as the vascular region of the meniscus and the ACL. The vascular supply should also be generally beneficial for the formation of new tissues, even those that do not require a vascular supply after they mature. Some tissues, such as cartilage, are vascularized during embryonic development, but a vascular in the adult.

Figure 2:
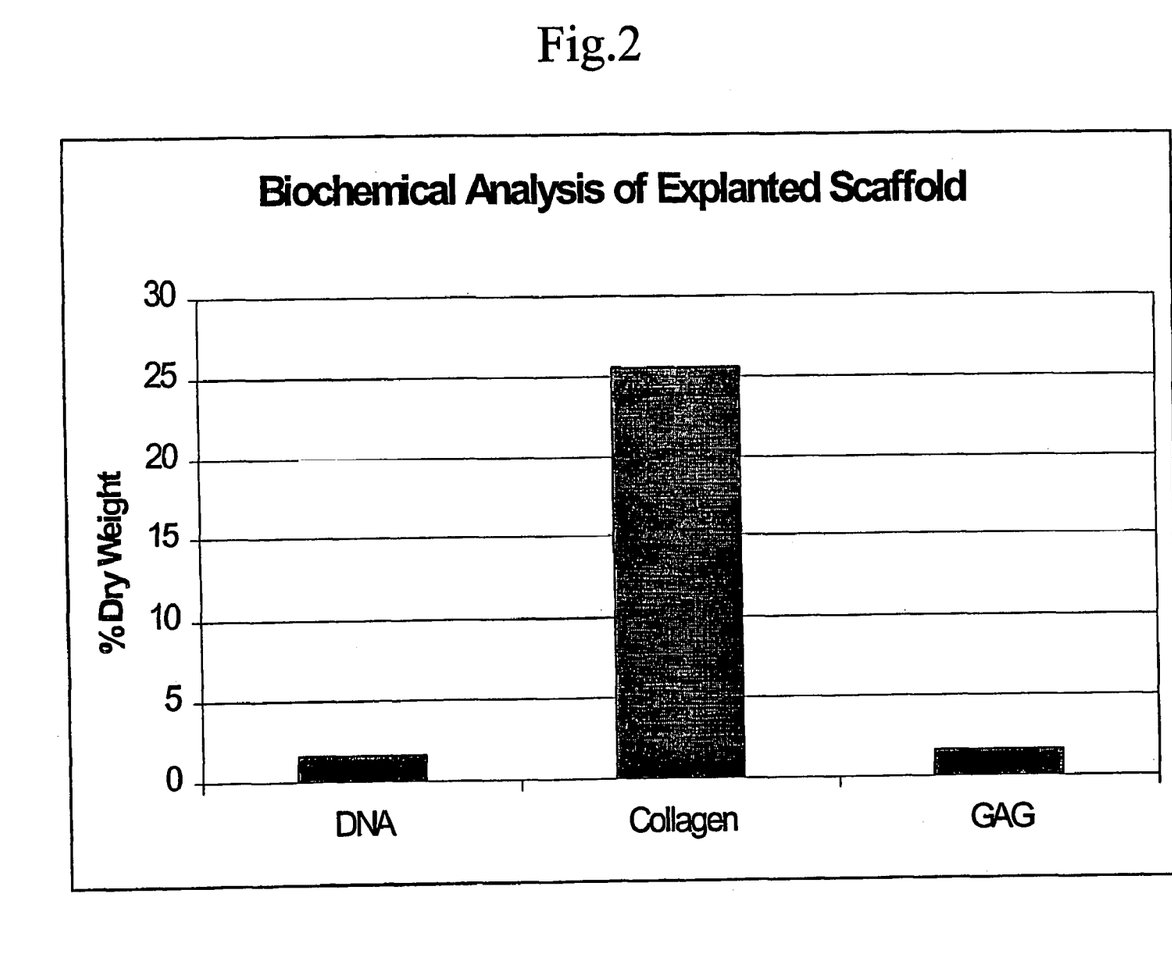
FIG. 2 is a bar graph illustrating the results of a biochemical analysis of the scaffold shown in FIG. 1 (% dry weight of DNA, collagen, and GAG).
Figure 3A:
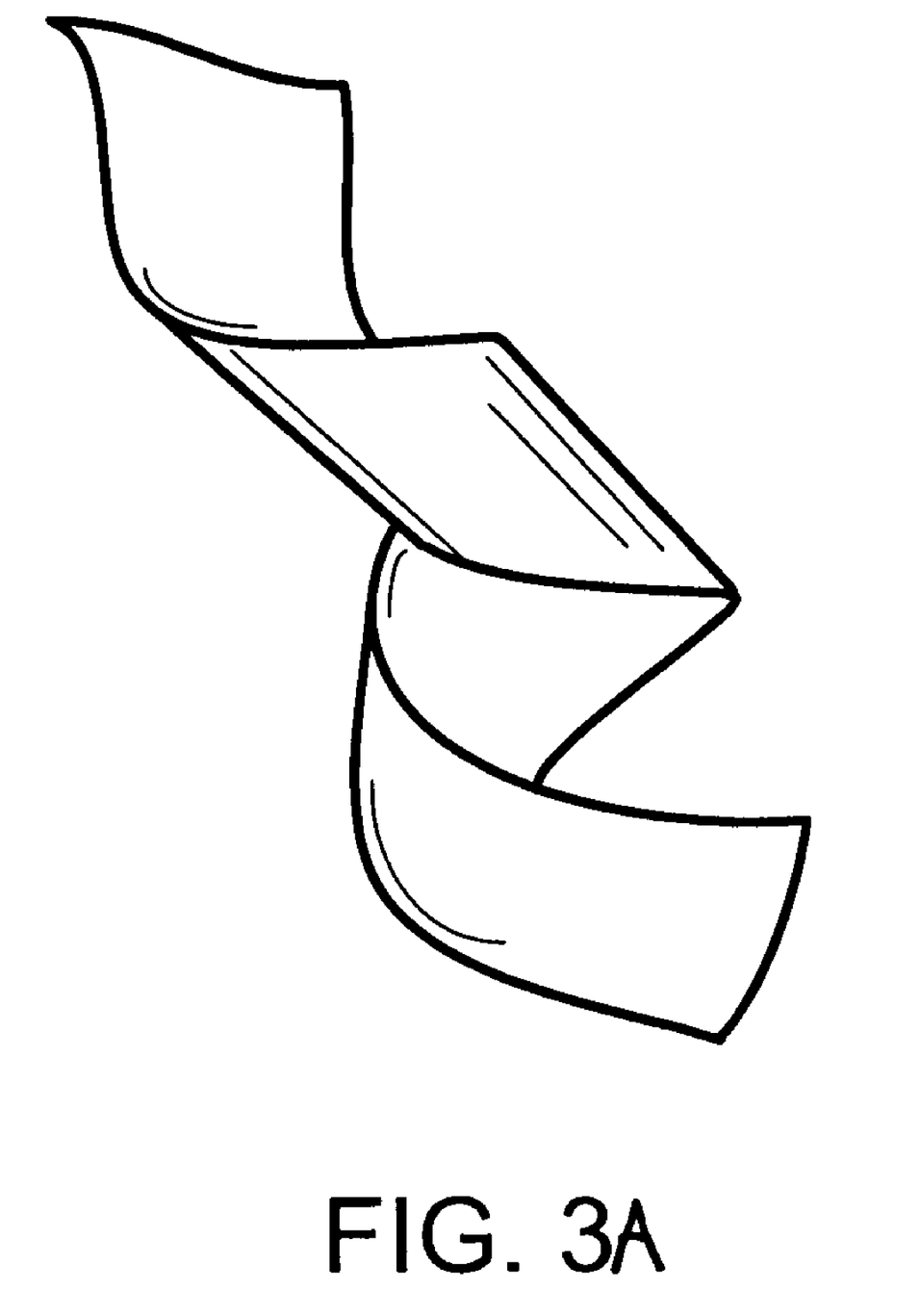
FIGS. 3A and 3B are illustrations of a planar scaffold that is helically wound.
Figure 3B:
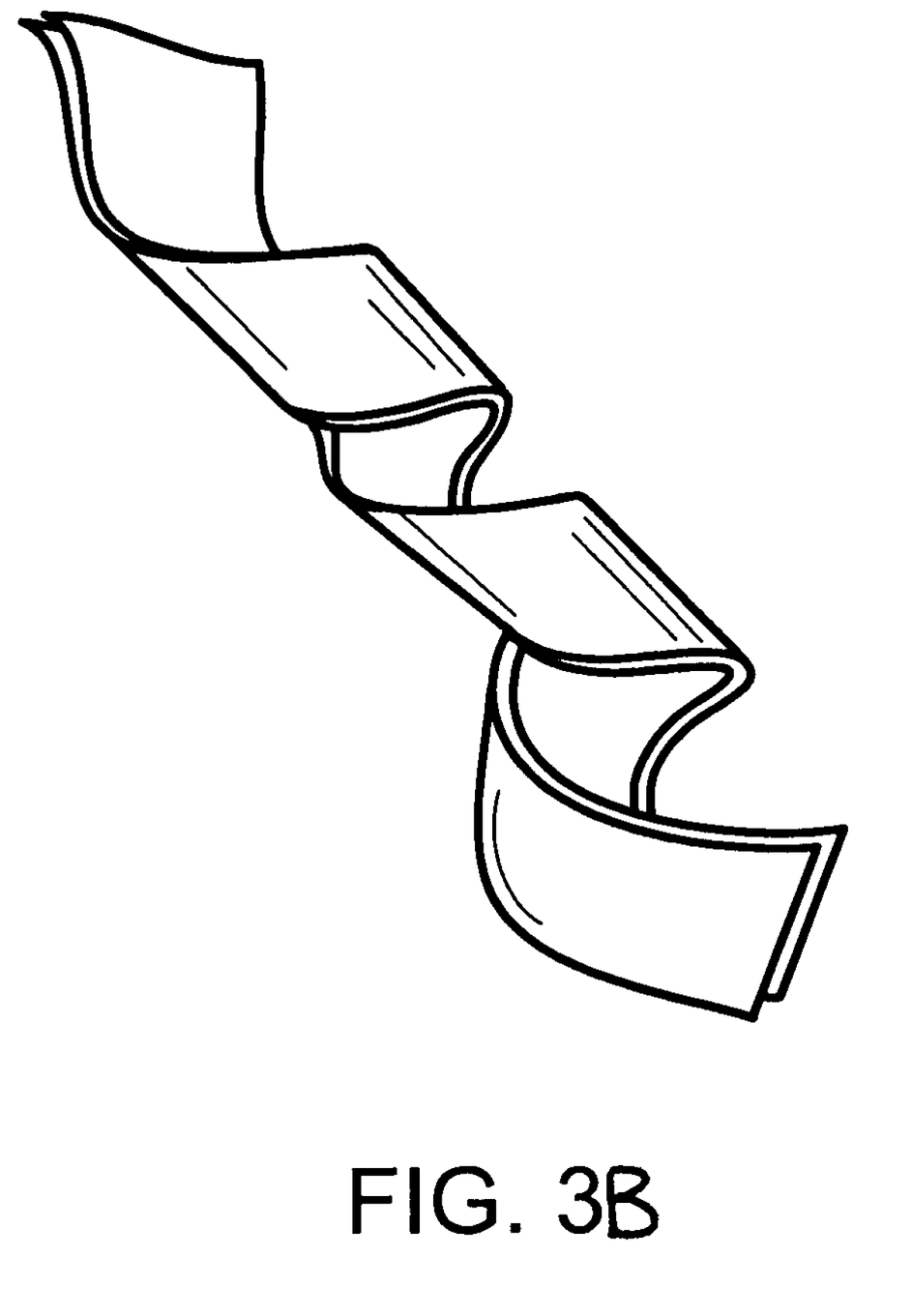

The explanted graft shown in FIG. 1 was analyzed biochemically, and the weights of various components of the tissues that grew on (or into) the scaffold are shown in FIG. 2. The components measured were DNA, collagen, and glycosaminoglycans (GAGs), and the weights of these components are shown as a percentage of the dry weight of the scaffold. This analysis supports the histological observation that significant tissue ingrowth occurred; about 27% of the dry weight of this graft is made up of the ingrown tissue.

EXAMPLE 3

Tissue Regrafting

In this series of experiments, the scaffolds manufactured as described in Example 1 were implanted into a mammal, removed eight weeks later, then regrafted into a second site in the same mammal. The regrafted tissue was removed three months later. Three female sheep that were approximately two years old and weighed between 55 and 80 kg were used for these studies.

Anaesthsia: Long acting amoxycillin (Clamoxyl LA 150 mg/ml) was obtained from Pfizer Ltd. and administered by intramuscular injection at a dose of approximately 15 mg/kg at the time of surgery and two days post surgery. Anaesthesia was induced with injectable 5% Thiopentone sodium (Intraval Sodium; Rhone Merieux Ltd) administered 'to effect' by rapid intravenous injection at an approximate dose of 15 mg/kg. Following induction, the animals were intubated with an appropriately sized endotracheal tube, and anaesthesia was maintained with a mixture of halothane, oxygen, and nitrous oxide.

Implantation procedure: Under aseptic conditions, scaffolds manufactured as described in Example 1 were implanted into the lateral aspect of the stifle joint as close as possible to the patellar tendon. Small skin incisions were created at each end of the proposed implantation site and a subcutaneous 'tunnel', joining the two incisions, was created by blunt dissection. The tunnel lay adjacent to the patellar tendon. The scaffold was soaked in physiological saline and threaded into the tunnel. Non-resorbable sutures anchored each end of the scaffold to the surrounding tissues to prevent dislodgement and to allow differentiation of the scaffold/graft from the surrounding tissues at the time of harvest. The surgical incisions were closed in a standard manner, and sutures were removed approximately 10 days later. Recovery was uneventful.

Harvest of grafts and implantation into the joint: Grafts (i.e. the scaffold including laid-down tissue) were harvested eight weeks after they were initially implanted and, during the same surgical procedure, grafted into a joint. The animals were anaesthetized as described above.

To harvest the graft, an incision was made under aseptic conditions along the course of the implanted scaffold. The graft was harvested by blunt dissection and stored in physiological saline until an implantation/graft site was prepared.

The lateral parapatellar incision that was used to harvest the implant was also used to expose the graft site in the knee joint. The patella was dislocated medially, and the stifle joint was assessed visually to ensure the absence of gross pathology (e.g., degenerative joint disease). The stifle joint was flexed to expose the ACL, which was resected as close to its origin and insertion sites as possible. All visible particulate matter was removed from the joint, and the joint was flushed with sterile physiological saline.

Using an adapted, standard orthopaedic drill guide, a Kirschner wire (K-wire) was inserted from the medial border of the proximal tibia (approximately 1 cm distal to the joint surface and midway between anterior and posterior aspects of the tibia) and directed into the joint at the point of insertion of the resected ACL. An appropriately designed drill bit was slipped over the K-wire, and a suitable bone tunnel, extending into the joint, was created. All resultant visible debris was removed, and the articular borders of the bone tunnel were smoothed to reduce abrasion of the implant.

An orthopaedic cruciate 'hook' was inserted between the femoral condyles and directed posteriorly toward the caudo-lateral aspect of the lateral condyle to exit lateral and proximal to the lateral fabella. The 'hook' was used to guide a graft passer into the joint from the lateral aspect of the lateral condyle, around the posterior of the lateral condyle to exit in the inter-condylar space. Using the graft passer, the implant was inserted from the anterior aspect of the inter-condylar space, between the condyles and around the caudo-lateral aspect of the lateral condyle to exit at the disto-lateral femur.

The femoral end of the implant was anchored to the disto-lateral femur with standard orthopaedic screws and washers. Using a graft passer, the tibial end of the implant was passed from the joint space into and through the tibial tunnel. The tibial end of the implant was tensioned to ensure it had been inserted fully and was then anchored with standard orthopaedic RCI (round head cannulated inside-out) screws, which were inserted into the tunnel from the medial aspect of the tibia and directed towards the joint.

The patella was relocated, and the limb was manipulated through the full range of normal motion approximately five times. The intra-articular portion of the ligament was assessed for taughtness. Following implantation to the satisfaction of the surgeon, excess implant length was removed from the medial aspect of the tibia. The patella was relocated and the incisions sutured in the standard surgical manner. Robert-Jones type dressings were applied and maintained for approximately seven days post surgery. Analgesia (buprenorphine—Vetergesic; Animalcare) was administered at completion of surgery and maintained for a minimum of 48 hours post surgery. Antibiotic cover was maintained for four days.

Following recovery from the surgical procedures, the animals were individually housed for a minimum of seven days and then group housed until they were returned to pasture at approximately 5 weeks after surgery. All skin sutures (including resorbable sutures) were removed at 10 to 14 days post surgery or once healing had occurred. Animals were clinically observed during the recovery period. Recovery of the animals was uneventful in all cases.

Gross Pathology: At three months, all three animals that received an ACL graft (as described above) were walking normally, with stable joints at termination. Apart from a few adhesions, there was minimal joint pathology. The grafts were intact with substantial amounts of tissue around them and within them.

Mechanical Testing: At three months, joint explantations were performed, the joints were stored overnight at approximately 4° C., and then allowed to warm to ambient temperature before testing the following day. To mount the joints without exerting external forces on the ligaments within them, it was necessary to mount the joints into the in-situ testing apparatus before dissection (so that the ovine joint was in its natural fully extended position of 30° flexion). It was necessary to dissect away the muscle bulk surrounding the joint before placing it in the testing apparatus. Once the joint was clamped into position, the dissection was completed, leaving only the ACL or graft in position. Testing was performed using an INSTRON™ 8511 servo-hydraulic test machine with either a 1 kN dynamic load cell or a 20 kN static load cell. The test was performed in displacement control at a rate of 10 mm/min.

The average final failure load for the three "regrafted" ligaments was 64% higher than it was for scaffolds that were otherwise identical to those described in Example 1 but had not been implanted into the animals' bodies first to allow tissue to become associated with them.

Biochemistry: All graft sections were freeze-dried overnight, and then digested by exposure to papain at 60° C. The papain solution, which contained the digested sample, was separated from the residual scaffold material and used for an analysis of the total amount of collagen.

As the weight of dried scaffold remaining after tissue digestion contributes significantly to the total dry sample weight, the residual scaffold material was dried and reweighed. This figure was deducted from the total sample dry weight to obtain a nominal dry weight attributable to the new tissue component of the samples.

The total tissue within the scaffold was found to increase following the "regrafting" procedure. When initially obtained, the graft contained 44% tissue, but following "regrafting" into the ACL site for three months, the graft contained 58% tissue. This compares with the control value of 48%. The quality of the tissue also increased, as indicated by the total amount of collagen within it. When initially obtained, the graft contained 26% collagen, but following "regrafting" into the ACL site for three months, the graft contained 42% collagen. In comparison, the control value was 36%.

EXAMPLE 4

Grafts Obtained by Implanting Scaffold over Cartilage

A sheet of scaffold material was surgically placed under the perichondrium surrounding the costal cartilage of the ribs. A linear incision was made in the perichondrium, which was then carefully dissected way from the underlying cartilage to create a pocket between the perichondrium and the costal cartilage. The scaffold was then inserted into the pocket. The linear incision in the perichondrium was closed with sutures, and the animals were housed to allow normal functional locomotion for a post-operative period of eight weeks. The resulting grafts were then harvested for implantation into defects on the articular cartilage of the femoral condyle of the knee joint.

EXAMPLE 5

Grafts Obtained by Implanting Scaffold over a Meniscus

Semicircular meniscal shaped scaffolds were placed over (i.e., adjacent to) the patellar tendon of the knee joint A stab incision was created through the skin above the patella tendon with a scalpel. A curved hook was then forced over the top of the patella tendon to form a semicircular tunnel. A second incision was then created with the scalpel to allow the point of the hook to exit through the skin at the end of the tunnel opposite the insertion site. The scaffold was pulled into place within the tunnel using the hook so that it was positioned along the patellar tendon via a semicircular tunnel. The scaffold was then sutured onto the patellar tendon at either end of the incision, and the wounds were closed. The animals were housed to allow normal functional locomotion for a post-operative period of eight weeks. The resulting grafts (i.e., scaffold and associated tissue) were then harvested for replacement of degenerative meniscal tissue within the knee joint.

EXAMPLE 6

Grafts Obtained by Implanting Scaffold over Bone

In this series of experiments, a scaffold was inserted under the periosteum of the tibia. The tibia was accessed through an incision of the skin covering the shin. The tissue surrounding the periosteum of the tibia was carefully dissected. A linear incision was made in the periosteum, and the periosteum was dissected way from the underlying cortical bone to form a pocket into which the scaffold was placed. Prior to inserting the scaffold, 2×2 mm holes were drilled, within the pocket, through the cortical bone into the marrow space to allow passage of cells from the bone marrow into the scaffold. The scaffold was inserted into the pocket between the periosteum and cortical bone. The linear incision in the periosteum was then closed at either end using sutures. The animals were housed as to allow normal functional locomotion for a post-operative period of 4 weeks. The resulting grafts (i.e. scaffold and associated tissue) were then harvested for implantation into bone defects.

EXAMPLE 7

Manufacture and Implantation of a PET Scaffold; Surgical Removal and Implantation of the Graft Generated thereby Felt Manufacture: Polyethylene terephthalate (PET) multifilament flat yarn (of 50 dTex/20 filaments; 2.5 dTex per filament) having circular filaments was used. The yarn was plied up to produce a tow of 550–600 dTex, which was fed into a stuffer box type crimping unit. The crimper line speed was 300 m/min, and the yarn was heated by passing it around a godet roller that was maintained at 126° C. 26 times. The yarn in the column of the stuffer box was controlled at a height of 40 cm and a temperature of 45° C. A batch of 570 g of crimped yarn was produced, with a crimp frequency of 20 per inch. The crimped yarn was chopped to give a staple fibre length of 50 mm.

The fibre was processed to produce needled felt: a 165 gsm carded bat was needled for 5 passes with 200 penetrations/cm$^2$/pass, having a 6 mm penetration depth and giving a felt of 2.2 mm thickness, and a density of 60 mg/cm$^3$. This was then platen pressed at 180° C. for 5 minutes with 2.15 mm spacers to produce a felt of 1.85 mm thickness and a density of 93 mg/cm$^3$.

The felt was washed repeatedly in purified water at 60 to 70° C. and spun dry. The washing and spin-drying were continued until there was no further frothing (9 to 12 times), and the felt was then given a final wash in propan-2-ol and vacuum-dried at 115° C., 980 mbar for 15 hours. The felt was then cut into discs using a multiple 12 mm diameter rule cutter.

PCL Coating: The felts were impaled on syringe needles (Microlance 3, 0.8×50) and immersed in 2% PCL solutions for at least 30 seconds. The syringe needles were mounted on jar caps, which were then screwed onto 250 ml glass jars. The jars (and felts) were placed on roller mixers and rotated at 50 rpm. The aim of this procedure was to retain an even distribution of PCL by preventing the solution from draining to the lowest point. After 15 minutes, the caps were briefly removed to vent the jars, and the rolling was resumed. This was repeated at 15-minute intervals until the felts were roughly dried. The purpose was to restrict the rate of drying and thereby avoid the PCL being blown by the solvent. The implants were then fully dried in a vacuum oven at 55° C. and 900 mbar for 16 hours. The felts were sterilized by ethylene oxide treatment and the packs were vacuum degassed as a precaution against any residual EtO. The sterilisation processes did not change the dimensions of the scaffolds.

Scaffolds: The resulting scaffolds were discs having a diameter of 12 mm and a thickness of 1.85 mm. In addition, the felts contained 25.4% gPCL/gPET, they had a volume of 0.21 cm$^3$ and a density of 120 mg/cm$^3$.

Surgical implantation of scaffolds and harvest of implants: Long acting amoxycillin (Clamoxyl LA 150 mg/ml; Pfizer Ltd) was administered by intramuscular injection to six adult sheep, at a dose of approximately 15 mg/kg at the time of surgery and two days afterward (as recommended by the manufacturer). Thereafter, amoxycillin was given as required. Premedication was provided by intramuscular injections of acepromazine (ACP 10 mg/ml) and buprenorphine (0.3 mg/ml). ACP was administered at a dose rate of approximately 0.01 mg/kg, 10–60 minutes prior to induction of anaesthesia. Buprenorphine analgesia was administered at a dose rate of 0.005 mg/kg at the same time as the ACP. 5% thiopentone sodium (Intraval Sodium; Rhone Merieux Ltd.) was administered 'to effect' by intravenous injection at an approximate dose of 10 mg/kg. Anaesthesia was maintained using a mixture of halothane, oxygen, and nitrous oxide.

The periosteum on the proximal tibia was exposed in the six sheep, and a pocket was created between the periosteum and the tibia. Scaffolds, manufactured as described above, were implanted into the pocket, and the periosteum was sutured to close the opening holding the scaffold in place. The muscle, fascia, subcutaneous tissue and skin were closed using standard surgical procedures. The resulting implant was harvested 4 weeks post implantation and the wounds closed, as above. This graft was used to repair an articular cartilage defect.

Repair of articular cartilage using harvested implants: Under aseptic conditions, and using a standard surgical approach, articular cartilage was exposed. A cylindrical defect (10 mm diameter, 2 mm deep) was created in the articular cartilage on the medial condyle, using standard instrumentation. The site was cleaned and examined. The graft, which was slightly oversized (10.2 mm diameter, 2 mm deep), was sutured in place. The joint capsule, muscle, fascia, subcutaneous tissue and skin were closed in a standard surgical manner. Twelve weeks later, all six animals were euthanased, and the stifle joints were removed for histological analysis.

Histological analysis: Excised samples were fixed in formalin, decalcified in 8% formic acid, and processed into paraffin wax. Wax blocks were sectioned at approximately 5 μm and air-dried on microscope slides overnight. Sections were stained using haematoxylin and eosin (H&E) and safranin O.

Results: One month after scaffolds were implanted under the periosteum, they were incorporated with a loose fibrous tissue and cell morphology indicated that the majority of cells were fibroblasts. Giant cells were also observed, generally on the surface of the scaffold. Associated tissue was largely in the form of a dense tissue layer along one surface, with the opposite surface demonstrating areas of bone growth. Three months post "regrafting" into osteochondral cartilage defects, the grafts (i.e. the scaffold and associated cells and tissue) were incorporated into the defects and contained a heterogeneous tissue with varied cellularity and matrix deposition. There were areas of hyaline cartilage that were apparent within the scaffolds (characterised by chondrocytes surrounded by dense, extracellular matrix) that stained intensely for glycosaminoglycans. These results demonstrate that the methods described herein can be used to stimulate repair of articular cartilage defects.

A number of embodiments of the invention have been described. Nevertheless, it will be understood that various modifications may be made without departing from the spirit and scope of the invention.

What is claimed is:

1. A method for generating a tissue graft, the method comprising
   (a) implanting into a mammal a biocompatible scaffold comprising an elongated fabric tape comprising poly (lactic acid) fibres and a non-woven felt comprising poly(glycolic acid) fibres, wherein the scaffold is in direct contact with, or adjacent to, target tissue for a time sufficient to allow cells of the target tissue to associate with the scaffold, thereby forming a tissue graft; and
   (b) removing the tissue graft from the mammal.

2. The method of claim 1, wherein the scaffold has an open volume that is approximately 30–99% of the total volume of the scaffold.

3. The method of claim 1, wherein the scaffold further comprises a polypeptide growth factor.

4. The method of claim 3, wherein the growth factor is a transforming growth factor, a bone morphogenetic protein (BMP), a cartilage-derived morphogenic protein, a growth differentiation factor, an angiogenic factor, a platelet-derived growth factor, vascular endothelial growth factor, an epidermal growth factor (EGF), a fibroblast growth factor, a hepatocyte growth factors, an insulin-like growth factors, a growth hormone, an interleukin, a connective tissue growth factor, or a parathyroid hormone-related protein.

5. The method of claim 1, wherein the non-woven felt is stitched onto one of the surfaces of the fabric tape and the resulting structure helically wound.

6. The method of claim 1, wherein the scaffold, prior to implantation, bears no cells.

7. The method of claim 1, wherein the scaffold, following removal from the mammal, is suitable for use as a graft without the addition of any other cell type.

8. A tissue graft obtained by a method comprising:
(a) implanting into a mammal a biocompatible scaffold comprising an elongated fabric tape comprising poly(lactic acid) fibres and a non-woven felt comprising poly(glycolic acid) fibres, wherein the scaffold is in direct contact with, or adjacent to, target tissue for a time sufficient to allow cells of the target tissue to associate with the scaffold, thereby forming a tissue graft; and
(b) removing the tissue graft from the mammal.

9. A method of treating a mammal that has a tissue defect, the method comprising implanting the tissue graft of claim 8 into the mammal at the site of the tissue defect.

10. The method of claim 9, wherein the mammal that has the tissue defect and the mammal from which the tissue graft is obtained are the same mammal or the same type of mammal.

11. The method of claim 9, wherein the mammal that has the tissue defect and the mammal from which the tissue graft is obtained are different types of mammals.

12. The method of claim 9, wherein implanting the tissue graft comprises suturing, pinning, tacking, or stapling the tissue graft into the mammal at the site of the tissue defect.

13. The method of claim 9, wherein the target tissue is a tendon, ligament, cartilage, or bone.

14. The method of claim 9, wherein implanting the tissue graft comprises attaching a first portion of the graft to a first support structure at the site of the tissue defect and attaching a second portion of the graft to a second support structure at the site of the tissue defect, such that the graft connects the first support structure to the second support structure.

15. The method of claim 14, wherein the first support structure is the tibia and the second support structure is the femur.

16. The method of claim 15, wherein the tissue defect comprises a defect of a natural cruciate ligament or a natural collateral ligament.

17. The method of claim 14, wherein the first support structure is a first articular surface of a knee joint and the second support structure is a second articular surface of a knee joint.

* * * * *

UNITED STATES PATENT AND TRADEMARK OFFICE
CERTIFICATE OF CORRECTION

| | | |
|---|---|---|
| PATENT NO. | : 7,108,721 B2 | Page 1 of 1 |
| APPLICATION NO. | : 10/275618 | |
| DATED | : September 19, 2006 | |
| INVENTOR(S) | : James William Huckle et al. | |

It is certified that error appears in the above-identified patent and that said Letters Patent is hereby corrected as shown below:

Title page, col. 1, section (73), add a second Assignee -- Smith & Nephew, Inc., Memphis TN --.

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,108,721 B2 |
| APPLICATION NO. | : 10/275618 |
| DATED | : September 19, 2006 |
| INVENTOR(S) | : James William Huckle et al. |

It is certified that error appears in the above-identified patent and that said Letters Patent is hereby corrected as shown below:

Cover page, col. 1, section (73), add a second Assignee -- Smith & Nephew, Inc., Memphis TN --.

Signed and Sealed this

Ninth Day of December, 2008

JON W. DUDAS
*Director of the United States Patent and Trademark Office*